United States Patent [19]

Brizzolara

[11] Patent Number: 5,858,801
[45] Date of Patent: Jan. 12, 1999

[54] PATTERNING ANTIBODIES ON A SURFACE

[75] Inventor: Robert A. Brizzolara, Beltsville, Md.

[73] Assignee: The United States of America as represented by the Secretary of the Navy, Washington, D.C.

[21] Appl. No.: 816,337

[22] Filed: Mar. 13, 1997

[51] Int. Cl.$^6$ .............................. C08J 7/04; G01N 33/543
[52] U.S. Cl. .................... 436/518; 430/302; 430/304; 430/298; 430/297; 430/299; 422/57; 422/60; 435/33; 435/287.8; 435/287.9; 435/973; 436/527; 427/2.11; 427/2.13; 427/466; 427/470; 427/504; 427/534; 427/288; 427/286
[58] Field of Search ...................................... 430/302, 304, 430/298, 297, 299; 422/57, 60; 435/33, 287.8, 287.9, 973; 436/518, 527; 427/2.11, 2.13, 466, 470, 504, 534, 288, 286

[56] References Cited

U.S. PATENT DOCUMENTS

| | | |
|---|---|---|
| 3,941,876 | 3/1976 | Marinkovich . |
| 3,960,490 | 6/1976 | Giaever . |
| 4,011,308 | 3/1977 | Giaever . |
| 4,011,350 | 3/1977 | Markovits et al. . |
| 4,092,116 | 5/1978 | Giaever . |
| 4,157,895 | 6/1979 | Finlay et al. . |
| 4,259,433 | 3/1981 | Mizobuchi et al. . |
| 4,262,186 | 4/1981 | Provancher . |
| 4,417,948 | 11/1983 | Mayne-Banton et al. . |
| 4,591,570 | 5/1986 | Chang . |
| 4,764,485 | 8/1988 | Loughran et al. . |
| 4,826,755 | 5/1989 | Garbassi et al. . |
| 5,391,463 | 2/1995 | Ligler et al. . |
| 5,512,492 | 4/1996 | Herron et al. . |
| 5,516,703 | 5/1996 | Caldwell et al. . |
| 5,643,472 | 7/1997 | Engelsberg et al. . |

OTHER PUBLICATIONS

Brizzolara, Robert. A method for patterning purple membrane using self–assembled monolayers, Journal of Biological and Information Processing Sciences. 35(1):137–140, 1995.

Brizzolara et al. Control of purple membrane adsorption to a glass surface using self–assembled monolayers. J. Vac. Sci. Technol. 12(5):2981–2987,1994.

Lee et al. Protein–resistant surfaces prepared by PEo–containing block copolymer surfactants. Journal of Biomedical Materials Research. 23:351–368, 1989.

Primary Examiner—Christopher L. Chin
Assistant Examiner—Bao-Thuy L. Nguyen
Attorney, Agent, or Firm—John Forrest; Roger D. Johnson

[57] ABSTRACT

A patterned multiple antibody substrate for use in biosensors or immunosensors is produced by (1) coating an antibody-adsorbent substrate with a material that resists antibody adsorption, (2) using ion beam sputtering, laser ablation, or mechanical scribing to remove the coating at specific sites on the substrate, and then (3) adsorbing specific antibodies at the sites. The substrate is capable of detecting multiple chemical species simultaneously.

72 Claims, 3 Drawing Sheets

PATTERNING ANTIBODIES ON A SURFACE

BACKGROUND

Because of their exquisite specificity, biological molecules, including antibodies, have been employed in biosensors. Biosensors are devices capable of identifying and quantifying a target chemical. Biosensors are highly sensitive to their analyte (the chemical species to be detected—for an antibody-based biosensor, the analyte is the antigen to the antibody). They are able to detect quantities as small as $10^{-15}$ gram. They are also extremely specific toward the analyte because of the unique ability of the antibodies to recognize their target species at the molecular level.

The present state of the art in antibody-based biosensors is illustrated by the various commercially available immunoassays. An immunoassay is a chemical test based on the use of antibodies to bind the molecule to be detected. In these assays, an antibody specific to the analyte (the "capture antibody") is immobilized onto a solid surface. This surface is then exposed to the sample to be analyzed and the immobilized antibodies bind some of the analyte present in the sample. After the surface is washed, it is immersed in a solution of a second antibody (the "signal antibody") specific to the same analyte. The signal antibody is conjugated (attached chemically) to a radioactive, fluorescent, or enzymatic label, so that it can be detected with high sensitivity. The amount of the signal antibody bound to the analyte is determined by the amount of radioactivity, intensity of fluorescence, or quantity of enzymatic reaction product, which in turn is proportional to the quantity of antigen in the sample. In the case of the enzyme label, the enzyme converts molecules of an added colorless reactant to colored reaction products. The intensity of the color change is read by a spectrophotometer. This type of assay is called ELISA (enzyme-linked immunosorbent assay). Examples of commercially available ELISA test kits are home pregnancy tests and environmental monitoring tests for BTEX (benzene, toluene, ethylbenzene, and xylene), PAH(polynuclear aromatic hydrocarbons) or PCB's (polychlorinated biphenyls) in water. ELISA assays are also used in the military for battlefield detection of chemical and biological warfare agents. A disadvantage of these immunoassay kits is that a separate kit is required for each antigen or closely related family of antigens being tested for. Not only is this costly and labor consuming when many antigens must be tested for, but it can also result in dangerous time delays as when chemical and biological warfare agents are being tested for on the battlefield.

It would be desirable to provide a single device that could perform multiple immunoassay tests at the same time. The test results of such a device would be read and evaluated automatically. In order to achieve this, each type of antibody must be precisely and discretely located on the test surface. Cross contamination of the antibodies must be avoided. Moreover, such devices should be inexpensive and easy to manufacture.

SUMMARY

Accordingly, an object of this invention is to provide a new device using multiple antibodies on a substrate to perform multiple immunoassay tests.

Another object of this invention is to provide a new device using multiple antibodies on a substrate to perform multiple immunoassay tests whose results can be read automatically.

A further object of this invention is to provide a new, inexpensive method of producing a device using multiple antibodies to perform multiple immunoassay tests.

Yet another object of this invention is to provide a new method of patterning multiple antibody types in discrete groups in precise locations.

These and other objects of this invention are achieved by providing a serial process for producing a multiple antibody patterned substrate by (1) coating an antibody-adsorbent substrate with an antibody-resistant material, (2) removing a portion of the antibody-resistant material to produce a bare site on the antibody-adsorbent substrate having a precise size, shape, and location on the substrate, (3) adsorbing molecules of a selected antibody on to the bare site on the antibody-adsorbent substrate, (4) rinsing the substrate to remove unadsorbed antibody molecules, (5) coating the antibody-adsorbent substrate with more of the antibody-resistant material to cover the bare surface of the substrate between the newly adsorbed antibody molecules, and (6) repeating steps (2) through (5) until each of the antibodies has been adsorbed at its specific site on the antibody-adsorbent substrate.

Alternatively, the multiple antibody patterned substrate is produced by a parallel process of (1) coating an antibody-adsorbent substrate with an antibody-resistant material that is resistant to the adsorption of antibodies, (2) removing portions of the antibody-resistant material to produce bare sites on the antibody-adsorbent substrate having precise sizes and shapes and each site having a precise location which corresponds to a specific antibody, (3) adsorbing molecules of each antibody to its specific bare site on the antibody-adsorbent substrate, (4) rinsing the substrate to remove unadsorbed antibodies, and (5) coating the antibody-adsorbent substrate with more of the antibody-resistant material to cover the bare surface of the substrate between the adsorbed antibody molecules.

Another aspect of this invention is a biosensing device having (A) an analyte-capturing structure comprising (1) an antibody-adsorbent substrate, (2) two or more antibodies adsorbed to the substrate, wherein each antibody is located at a specific site on the substrate apart from the other antibodies, and (3) an antibody-resistant material covering the substrate between the adsorbed molecules of the antibodies, and (B) means for determining the types and quantities of the analytes captured by the antibodies.

DESCRIPTION

Figure 1:
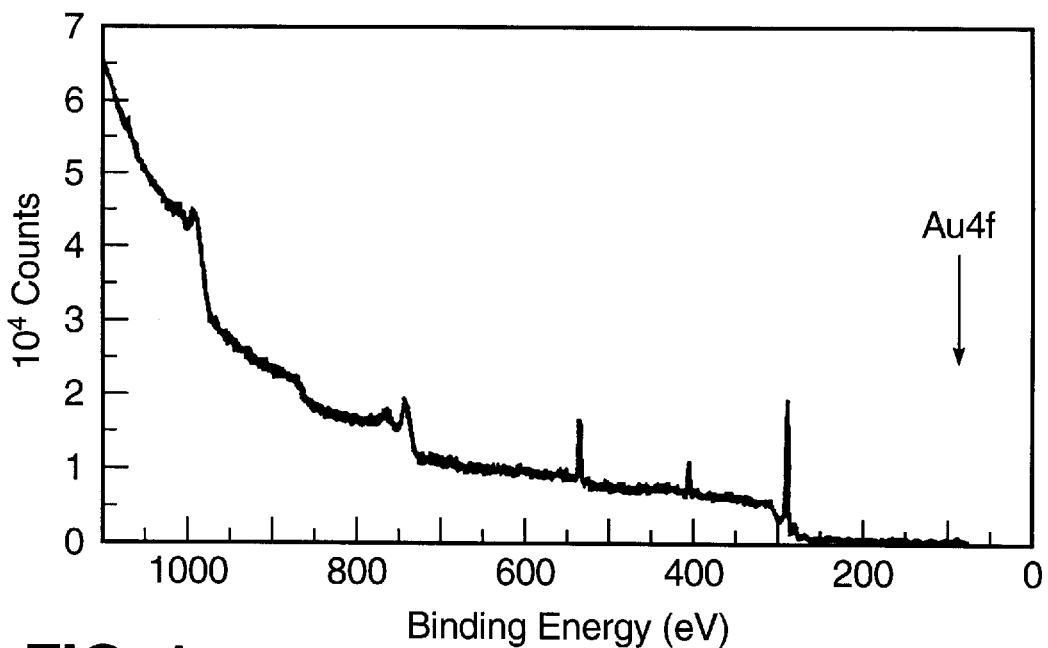
FIGS. 1, 2, 3, 4, and 5 show the x-ray photoelectron (XPS) spectra for substrate surfaces in examples 1 and 2 and are discussed in those examples.

The present invention provides method of producing biosensor substrates or chips having multiple antibodies patterned on them. Each antibody is present on the substrate in a specific amount and at a specific location. As a result the output of the substrate can be read automatically to identify and quantify the antigens or analytes present in a sample. The antibodies are separated from each other by an antibody-resistant coating on the substrate which reduces the danger of cross-reactivity between antibody sites and of nonspecific adsorption of antigen. Finally, the methods provide means of patterning many antibodies on a single substrate. This provides the device with the ability to detect multiple chemical species (analytes) or to detect a single species with multiple binding affinities, giving the device a wide range of response and reset times.

The multiple-antibody patterned substrate may be prepared by using either a serial process (as in the examples) or a parallel process. In the serial process, an antibody-adsorbent substrate is coated with an antibody-resistant material. The substrate is then placed in vacuum and an ion beam is used to sputter (etch) away the antibody-resistant coating to expose the surface of the antibody-adsorptive substrate at a selected area. Alternatively, a laser beam could be used to burn or ablate away the antibody-resistant coating to expose the surface. In still another variation, the antibody-resistant material could be precisely removed by mechanical scribing using atomic force microscopy. The substrate is then incubated in a first antibody which results in a large concentration of the first antibody adsorbing on the exposed surface of the antibody-adsorptive material and very little antibody adsorbing on the antibody-resistant coating. The substrate is then rinsed to remove any unadsorbed antibody while leaving the antibody adsorbed to the antibody-adsorbing substrate. Next the substrate is again coated with the antibody-resistant coating. This is a conventional procedure called blocking the surface and it results in any bare surface between the adsorbed antibody molecules being covered with antibody-resistant material. When the other antibodies are applied later they will not be able to attach to this area of the antibody-adsorbent substrate and contaminate it; also antigens will not be able to attach to this area of the substrate. The procedure is then repeated at a new site with a new antibody and this is continued until all the desired antibodies are on the substrate. A final antibody-resistant coating is applied to block the surface around the last antibody adsorbed.

Ion beam sputtering (etching) is used to remove the antibody-resistant coating and expose precise areas of antibody-adsorbent substrate at precise locations. This feature is critical to the production of automated biosensors. The shaping and positioning of the exposed areas may be achieved by using masks (as in the present examples) or by using a programmable ion beam sputtering device. Finally, note that the high spatial resolution of ion beams permits large numbers of antibody locations to be produced on the substrate. In an alternative embodiment, a laser beam is used to burn or ablate off the antibody-resistant coating in place of ion beam sputtering. Precise shaping and positioning of the exposed areas can be achieve by using masks with the laser or by using a programmable laser. Mechanical scribing using atomic force microscopy provides yet another method of precisely shaping and positioning the exposed areas.

On an industrial scale, it may be preferable to use a parallel process to produce the multiple antibody patterns on the substrates. An ion beam sputtering machine with masks or a programmable ion beam sputtering machine would be used to etch a large number of bare spots on the antibody-adsorbent substrate at once. Alternatively, a laser with a mask or a programmable laser could be used to ablate or burn off the antibody-resistant material from the antibody-adsorbent substrate at a large number of spots at one time. This could also be achieved by mechanical scribing using atomic force microscopy. In the next step, an array of micropipets could be used to deliver each antibody to the correct bare spot (site) and none other. The coating of antibody-resistant coating which separates the etched areas from each other is critical in this process to prevent the cross contamination of antibodies, or adsorption of the antigen in unwanted areas. Ink jet printing technology might be used in place of the micropipets. A final antibody-resistant coating is then applied to block or cover the bare substrate surface around each of the adsorbed antibody molecules. This step is necessary to prevent antibody contamination of the substrate during storage or use of the device, or to allow a false positive reading due to nonspecific antigen adsorption.

The antibody-adsorbent substrate may be composed of any material conventionally used to physically adsorb proteins or antibodies. The adsorption should be a spontaneous, physical process. In general, any hydrophobic material should be suitable for this purpose. Polystyrene (used in the examples) and polypropylene are the two most commonly used. However, many other hydrophobic polymeric materials such as polyethylene or copolymers of polyethylene and polypropylene will also work well. The use of cross-linking agents or other chemical agents to chemically bind the antibodies to the substrate are excluded from the processes of this invention.

The antibody-resistant coating is composed of a material which is resistant to antibody (protein) adsorption and which can be etched away in high yield and resolution by using ion beam sputtering or be ablated away by a laser beam, or be removed by mechanical scribing using atomic force microscopy. Examples of preferred antibody-resistant coatings include (1) bovine serum albumin, (2) gelatin, (3) lysozyme, (4) octoxynol, (5) Polysorbate 20 (polyoxyethylenesorbitan monolaurate), and (6) polyethylene oxide-containing block copolymer surfactants. Octoxynol can be represented by the formula

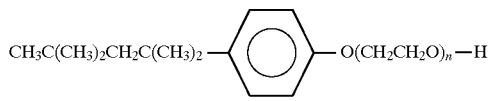

Wherein n is preferably from 9 to 10. The antibody-resistant polyethylene oxide-containing block copolymer surfactants include those containing polyethylene oxide-polypropylene oxide copolymer blocks and those containing polyethylene oxide-polybutylene oxide copolymer block. These surfactants are discussed by Jin Ho Lee et al. In "Protein-resistant surfaces prepared by PEO-containing block copolymer surfactants", *Journal of Biomedical Materials Research*, Vol. 23, pp. 351–368 (1989), herein incorporated by reference in its entirety. The more preferred antibody-resistant coatings are bovine serum albumin, gelatin, and lysozyme, with bovine serum albumin being the most preferred.

The multiple antibody patterned substrates of this invention function as multiple analyte or antigen capturing structures that are suitable for automatic analysis. Each analyte is identified by the position (site) of the antibody that captures it on the substrate. Conventional radioactive, fluorescent, or enzymatic labels can be used to mark the captured analytes for detection and measurement. The amount of radioactivity, intensity of fluorescence, or quantity of enzymatic reaction product (color change) is proportional to the quantity of the specific analyte captured by the specific antibody at the specific site. The quantity of analyte capture will be proportional to the concentration of the analyte present in the test environment (solution, air, blood, water, etc.) and the quantity of the capturing antibody present on the substrate at that site. The quantity of the antibody is controlled by the conditions under which the antibody was originally adsorbed on the antibody-adsorbent substrate and by the area of bare substrate available for antibody adsorption. The intensity of the label signals from the various sites on the substrate provides a complete picture of the concentrations of the analytes found in the test environment.

The general nature of the invention having been set forth, the following examples are presented as specific illustrations thereof. It will be understood that the invention is not limited to these specific examples but is susceptible to various modifications that will be recognized by one of ordinary skill in the art.

In examples 1 and 2, antibody R3631 (Sigma Chemical Company, St. Louis, Mo.) was used as the capture antibody. This is an antibody developed in sheep which is specific to (binds) rabbit antibody. The antigen was G5402 (Sigma Chemical Company). This is an antibody developed in rabbit which specificly binds goat antibody, and is conjugated to a 10 nm diameter gold particle. Thus, when R3631 is immobilized on a surface, it will bind G5402. Then, the gold label conjugated to G5402 can be detected by a number of techniques. In our laboratory, the presence of gold on a surface has been verified using optical absorption, XPS (x-ray photoelectron spectroscopy) and AFM (atomic force microscopy). The XPS technique yields the chemical composition of a surface (defined here as the uppermost 10 nm of a material). AFM is a high resolution microscopy. Optical Absorption, XPS and AFM all possess the necessary sensitivity to detect the presence of 10 nm gold particles.

EXAMPLE 1

The starting point for the fabrication of Sample #1 is a polystyrene substrate. Polystyrene surfaces are known to bind antibody molecules through hydrophobic interactions. Next, the polystyrene was coated by a protein, bovine serum albumin (BSA), known to inhibit the adsorption of antibody to a surface. This was done by immersing the polystyrene substrate in a solution of 1 gram of BSA in 100 ml of 0.01M phosphate buffered saline (PBS). Next, half of the surface was covered with a stainless steel mask and the unmasked half of the substrate was bombarded with energetic ions which, through momentum transfer, remove the BSA coating, exposing the underlying polystyrene. This process is known as sputtering. If the ion bombardment is confined to selected regions of the surface by using a lithographic mask or by tightly focusing and steering the ion beam, a surface with a differential affinity for antibodies will be created: the portions of the surface still coated with BSA resist antibody adsorption and the sputtered portions (BSA removed) bind antibodies to the surface.

The substrates were sputtered in the analysis chamber of a Physical Electronics 590 Scanning Auger Microprobe using a Physical Electronics Model 04-303 ion gun and Physical Electronics Model 11-065 ion gun controller. The base pressure of the system was $1 \times 10^{-10}$ torr, and the pressure during sputtering was approximately $1 \times 10^{-7}$ torr. The substrates were sputtered with 3 keV argon ions, a current density of approximately 1 $\mu$A/cm$^2$, for ten minutes. The patterned areas in were approximately 5 mm on a side. This was for demonstration purposes; ion beam lithography is capable of much high spatial resolutions. Additionally, the ion gun used was not capable of sputtering a pattern onto the substrate, thus a mask was used. Other ion guns exist that could be programmed to sputter a pattern onto the surface, thus eliminating the need for the mask.

Figure 2:
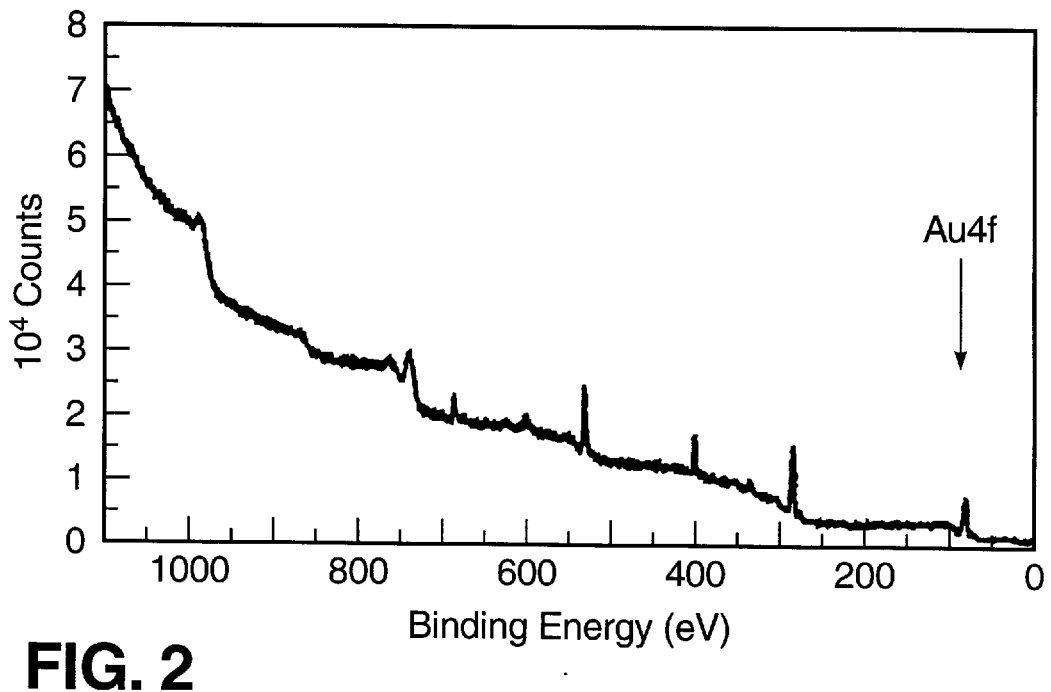

After sputtering, sample #1 was incubated at 37° C. for approximately 2 hours in a solution (approximate concentration 0.5 mg/ml) of the capture antibody, R3631, to bind it to its surface. Incubation is used to speed up the antibody-antigen binding. The goal in preparing sample #1 is to show that R3631 only binds to the sputtered half of the surface. To demonstrate this, the substrate was incubated in the antigen, G5402, which is conjugated to 10 nm diameter gold particles. When G5402 is immobilized on a surface, the Au particles can be detected by means of XPS or AFM. Both halves of the substrate were analyzed with XPS (FIGS. 1 and 2) and AFM. In the XPS spectrum, each peak signifies the presence of a different element on the surface of the substrate. The peak at about 80 eV is due to Au. The gold peak is barely evident in FIG. 1, the XPS spectrum from the unsputtered side of the substrate, but is clearly seen in FIG. 2, the sputtered side. The XPS results can be quantified on the basis of the areas under the various peaks—this is summarized in Table 1. The results show that there is a factor of 5 more gold on the sputtered half than on the unsputtered half of the substrate. These tests confirm that the 10 nm gold particles were present on the sputtered half of sample #1, but not the unsputtered half. The AFM images showed no gold particles on the unsputtered side, but gold particles appeared as circular features in AFM image of the sputtered side of the substrate. Thus the AFM results confirm the XPS finding that R3631 has bound to the sputtered side of the surface, but not to the unsputtered side. Control samples were also prepared that demonstrated that this was a specific antibody-antigen interaction and not nonspecific adsorption of G5402 to the surface. Thus this is a patterned, single antibody surface.

TABLE 1

|  | Sputtered Area No.1 Atomic % Au | Unsputtered Area Atomic % Au | Sputtered Area No.2 Atomic % Au |
|---|---|---|---|
| Sample 1 (example 1) | 1.5 + 0.1 | 0.3 + 0.2 | — |
| Sample 2 (example 2) | 1.4 | 0.4 | 1.2 |

EXAMPLE 2

Figure 3:
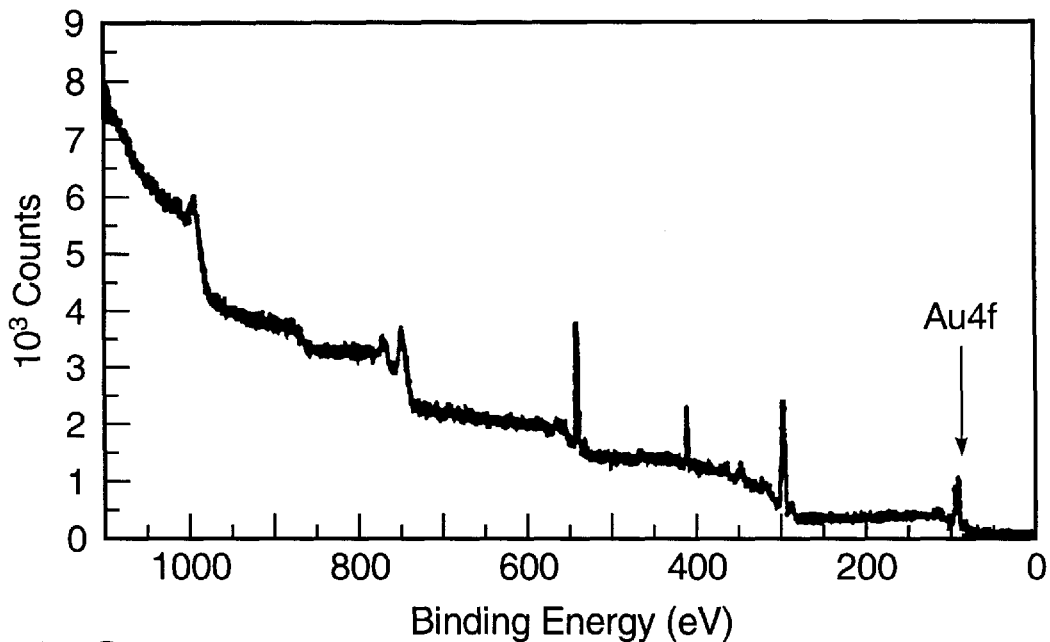
Figure 4:
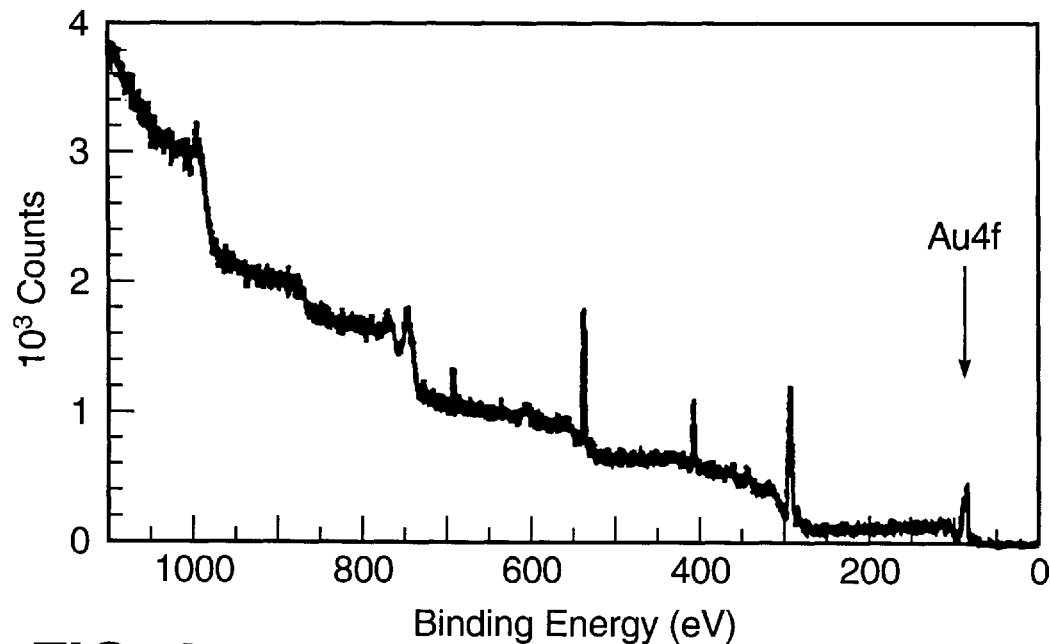
Figure 5:
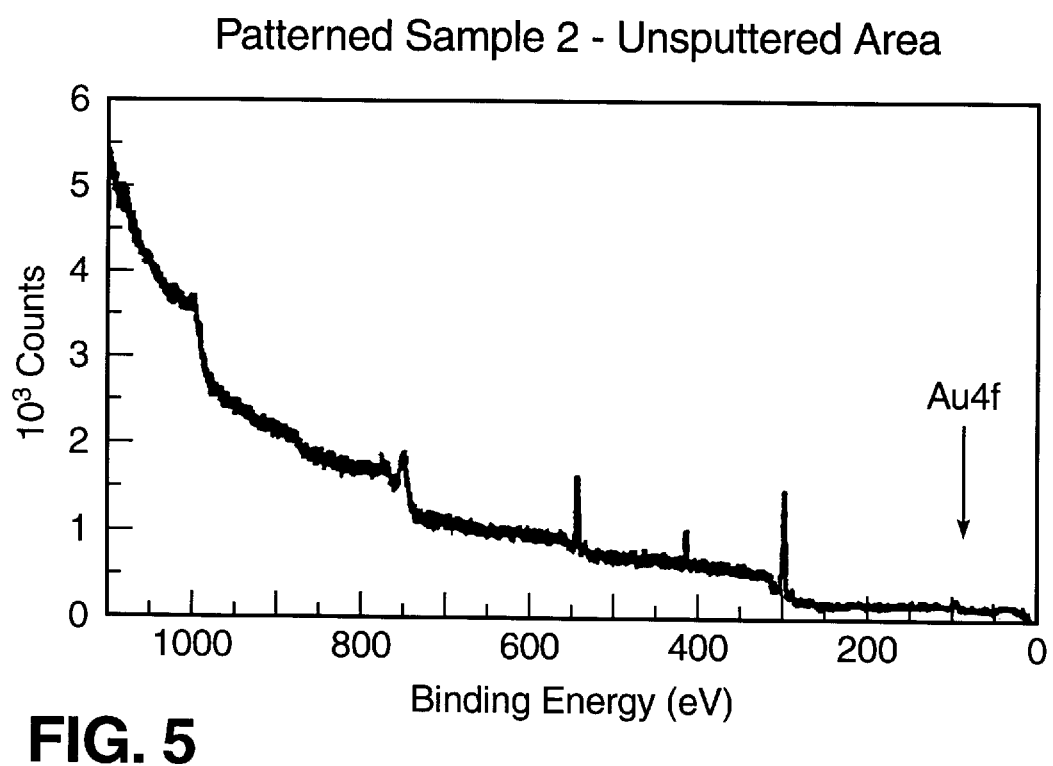

Sample #2 consisted of the R3631 antibody patterned sequentially onto two different areas of substrate. The surface of this substrate was lithographically divided into three equal size areas. Antibodies were immobilized sequentially onto the two outside areas, while the central area contained no immobilized antibody. The procedure was an extension of that for sample #1 (example 1). A polystyrene surface was coated with BSA. Then, a mask was used to cover two thirds of the substrate and the remaining third was sputtered using the same conditions as for sample #1. The substrate was then incubated in R3631, immobilizing the antibody on the sputtered area of the surface, but not on the unsputtered area. Now, a second, different area of the substrate was sputtered, and R3631 was immobilized on this area. The substrate was then exposed to a solution of G5402, the antigen/signal antibody. The XPS results, summarized in FIG. 3 (sputtered area No. 1), FIG. 4 (sputtered area No. 2), and FIG. 5 (unsputtered area) and Table 1 reveal that the G5402 is preferentially bound to the R3631 covered (sputtered) areas on the sample. There is a factor of 3.5 more gold on one sputtered section than on the unsputtered area and a factor of 3 more gold on the second sputtered section than on the unsputtered area. AFM could not be performed on this substrate due to constraints imposed by the sample geometry. This experiment demonstrates that antibody can be immobilized on a surface, in succession, using this method.

This procedure could easily be extended to patterning many antibodies onto a surface, in sequence, with each antibody specific to a different antigen. This is because antibodies to different antigens differ in structure on in their binding sites (which comprise a very small fraction of their total surface area), thus there is no difference in their affinity for various surfaces.

Obviously, other modifications and variations of the present invention may be possible in light of the foregoing teachings. It is therefore to be understood that within the scope of the appended claims the invention may be practiced otherwise than as specifically described.

What is claimed is:

1. A process for producing a multiple antibody patterned substrate comprising:
    A. coating an antibody-adsorbent substrate with an antibody-resistant material that is resistant to adsorption of antibodies;
    B. removing a portion of the antibody-resistant material to produce a bare site on the antibody-adsorbent substrate having a precise size, shape, and location on the substrate;
    C. adsorbing molecules of a selected antibody on to the bare site on the antibody adsorbent-substrate;
    D. rinsing the substrate to remove unadsorbed antibody molecules;
    E. coating the antibody-adsorbent substrate with more of the antibody-resistant material to cover the bare surface of the substrate between the newly adsorbed antibody molecules; and
    F. repeating steps B through E until each of the antibodies has been adsorbed at its specific site on the antibody adsorbent substrate.

2. The process of claim 1 wherein the antibody-adsorbent substrate is composed of a hydrophobic material.

3. The process of claim 2 wherein the antibody-adsorbent substrate is composed of a hydrophobic, polymeric material.

4. The process of claim 3 wherein the antibody-adsorbent substrate is composed of polystyrene, polypropylene, polyethylene, or copolymers of polypropylene and polyethylene.

5. The process of claim 4 wherein the antibody-adsorbent substrate is composed of polystyrene or polypropylene.

6. The process of claim 1 wherein the antibody-resistant material is bovine serum albumin, gelatin, lysozyme, octoxynol, polyoxyethylenesorbitan monolaurate, or a polyethylene oxide containing block copolymer surfactant.

7. The process of claim 6 wherein the antibody-resistant material is bovine serum albumin, gelatin, or lysozyme.

8. The process of claim 7 wherein the antibody-resistant material is bovine serum albumin.

9. A process for producing a multiple antibody patterned substrate comprising:
    A. coating an antibody-adsorbent substrate with an antibody-resistant material that is resistant to the adsorption of antibodies;
    B. removing portions of the antibody-resistant material to produce bare sites on the antibody-adsorbent substrate having precise sizes and shapes and each site having a precise location which corresponds to a specific antibody;
    C. adsorbing molecules of each antibody to its specific bare site on the antibody-adsorbent substrate;
    D. rinsing the substrate to remove unadsorbed antibodies; and
    E. coating the antibody-adsorbent substrate with more of the antibody-resistant material to cover the bare surface of the substrate between the adsorbed antibody molecules.

10. The process of claim 9 wherein each antibody adsorbed in step C is delivered to its precise bare site on the antibody-adsorbent substrate by micropipetting.

11. The process of claim 9 wherein each antibody adsorbed in step C is delivered to its precise bare site on the antibody-absorbent substrate by an ink jet printer.

12. The process of claim 9 wherein the antibody-adsorbent substrate is composed of a hydrophobic material.

13. The process of claim 12 wherein the antibody-adsorbent substrate is composed of a hydrophobic, polymeric material.

14. The process of claim 13 wherein the antibody adsorbent substrate is composed of polystyrene, polypropylene, polyethylene, or copolymers of polypropylene and polyethylene.

15. The process of claim 14 wherein the antibody-adsorbent substrate is composed of polystyrene or polypropylene.

16. The process of claim 9 wherein the antibody-resistant material is bovine serum albumin, gelatin, lysozyme, octoxynol, polyoxyethylenesorbitan monolaurate, or a polyethylene oxide containing block copolymer surfactant.

17. The process of claim 16 wherein the antibody-resistant material is bovine serum albumin, gelatin, or lysozyme.

18. The process of claim 17 wherein the antibody-resistant material is bovine serum albumin.

19. A process for producing a multiple antibody patterned substrate comprising:
    A. coating an antibody-adsorbent substrate with an antibody-resistant material that is resistant to adsorption of antibodies;
    B. removing a portion of the antibody-resistant material by ion beam sputtering to produce a bare site on the antibody-adsorbent substrate having a precise size, shape, and location on the substrate;
    C. adsorbing molecules of a selected antibody on to the bare site on the antibody adsorbent-substrate;
    D. rinsing the substrate to remove unadsorbed antibody molecules;
    E. coating the antibody-adsorbent substrate with more of the antibody-resistant material to cover the bare surface of the substrate between the newly adsorbed antibody molecules; and
    F. repeating steps B through E until each of the antibodies has been adsorbed at its specific site on the antibody adsorbent substrate.

20. The process of claim 19 wherein the antibody-adsorbent substrate is composed of a hydrophobic material.

21. The process of claim 20 wherein the antibody-adsorbent substrate is composed of a hydrophobic, polymeric material.

22. The process of claim 21 wherein the antibody-adsorbent substrate is composed of polystyrene, polypropylene, polyethylene, or copolymers of polypropylene and polyethylene.

23. The process of claim 22 wherein the antibody-adsorbent substrate is composed of polystyrene or polypropylene.

24. The process of claim 19 wherein the antibody-resistant material is bovine serum albumin, gelatin, lysozyme, octoxynol, polyoxyethylenesorbitan monolaurate, or a polyethylene oxide containing block copolymer surfactant.

25. The process of claim 24 wherein the antibody-resistant material is bovine serum albumin, gelatin, or lysozyme.

26. The process of claim 25 wherein the antibody-resistant material is bovine serum albumin.

27. A process for producing a multiple antibody patterned substrate comprising:
    A. coating an antibody-adsorbent substrate with an antibody-resistant material that is resistant to adsorption of antibodies;

B. removing a portion of the antibody-resistant material by laser ablation to produce a bare site on the antibody-adsorbent substrate having a precise size, shape, and location on the substrate;

C. adsorbing molecules of a selected antibody on to the bare site on the antibody adsorbent-substrate;

D. rinsing the substrate to remove unadsorbed antibody molecules;

E. coating the antibody-adsorbent substrate with more of the antibody-resistant material to cover the bare surface of the substrate between the newly adsorbed antibody molecules; and F. repeating steps B through E until each of the antibodies has been adsorbed at its specific site on the antibody adsorbent substrate.

28. The process of claim 27 wherein the antibody-adsorbent substrate is composed of a hydrophobic material.

29. The process of claim 28 wherein the antibody-adsorbent substrate is composed of a hydrophobic, polymeric material.

30. The process of claim 29 wherein the antibody-adsorbent substrate is composed of polystyrene, polypropylene, polyethylene, or copolymers of polypropylene and polyethylene.

31. The process of claim 30 wherein the antibody-adsorbent substrate is composed of polystyrene or polypropylene.

32. The process of claim 27 wherein the antibody-resistant material is bovine serum albumin, gelatin, lysozyme, octoxynol, polyoxyethylenesorbitan monolaurate, or a polyethylene oxide containing block copolymer surfactant.

33. The process of claim 32 wherein the antibody-resistant material is bovine serum albumin, gelatin, or lysozyme.

34. The process of claim 33 wherein the antibody-resistant material is bovine serum albumin.

35. A process for producing a multiple antibody patterned substrate comprising:

A. coating an antibody-adsorbent substrate with an antibody-resistant material that is resistant to adsorption of antibodies;

B. removing a portion of the antibody-resistant material by laser mechanical scribing using atomic force microscopy to produce a bare site on the antibody-adsorbent substrate having a precise size, shape, and location on the substrate;

C. adsorbing molecules of a selected antibody on to the bare site on the antibody adsorbent-substrate;

D. rinsing the substrate to remove unadsorbed antibody molecules;

E. coating the antibody-adsorbent substrate with more of the antibody-resistant material to cover the bare surface of the substrate between the newly adsorbed antibody molecules; and F. repeating steps B through E until each of the antibodies has been adsorbed at its specific site on the antibody adsorbent substrate.

36. The process of claim 35 wherein the antibody-adsorbent substrate is composed of a hydrophobic material.

37. The process of claim 36 wherein the antibody-adsorbent substrate is composed of a hydrophobic, polymeric material.

38. The process of claim 37 wherein the antibody-adsorbent substrate is composed of polystyrene, polypropylene, polyethylene, or copolymers of polypropylene and polyethylene.

39. The process of claim 38 wherein the antibody-adsorbent substrate is composed of polystyrene or polypropylene.

40. The process of claim 35 wherein the antibody-resistant material is bovine serum albumin, gelatin, lysozyme, octoxynol, polyoxyethylenesorbitan monolaurate, or a polyethylene oxide containing block copolymer surfactant.

41. The process of claim 40 wherein the antibody-resistant material is bovine serum albumin, gelatin, or lysozyme.

42. The process of claim 41 wherein the antibody-resistant material is bovine serum albumin.

43. A process for producing a multiple antibody patterned substrate comprising:

A. coating an antibody-adsorbent substrate with an antibody-resistant material that is resistant to the adsorption of antibodies;

B. removing portions of the antibody-resistant material by ion beam sputtering to produce bare sites on the antibody-adsorbent substrate having precise sizes and shapes and each site having a precise location which corresponds to a specific antibody;

C. adsorbing molecules of each antibody to its specific bare site on the antibody-adsorbent substrate;

D. rinsing the substrate to remove unadsorbed antibodies; and

E. coating the antibody-adsorbent substrate with more of the antibody-resistant material to cover the bare surface of the substrate between the adsorbed antibody molecules.

44. The process of claim 43 wherein each antibody adsorbed in step C is delivered to its precise bare site on the antibody-adsorbent substrate by micropipetting.

45. The process of claim 43 wherein each antibody adsorbed in step C is delivered to its precise bare site on the antibody-absorbent substrate by an ink jet printer.

46. The process of claim 43 wherein the antibody-adsorbent substrate is composed of a hydrophobic material.

47. The process of claim 46 wherein the antibody-adsorbent substrate is composed of a hydrophobic, polymeric material.

48. The process of claim 47 wherein the antibody adsorbent substrate is composed of polystyrene, polypropylene, polyethylene, or copolymers of polypropylene and polyethylene.

49. The process of claim 48 wherein the antibody-adsorbent substrate is composed of polystyrene or polypropylene.

50. The process of claim 43 wherein the antibody-resistant material is bovine serum albumin, gelatin, lysozyme, octoxynol, polyoxyethylenesorbitan monolaurate, or a polyethylene oxide containing block copolymer surfactant.

51. The process of claim 50 wherein the antibody-resistant material is bovine serum albumin, gelatin, or lysozyme.

52. The process of claim 51 wherein the antibody-resistant material is bovine serum albumin.

53. A process for producing a multiple antibody patterned substrate comprising:

A. coating an antibody-adsorbent substrate with an antibody-resistant material that is resistant to the adsorption of antibodies;

B. removing portions of the antibody-resistant material by laser ablation to produce bare sites on the antibody-adsorbent substrate having precise sizes and shapes and each site having a precise location which corresponds to a specific antibody;

C. adsorbing molecules of each antibody to its specific bare site on the antibody-adsorbent substrate;

D. rinsing the substrate to remove unadsorbed antibodies; and

E. coating the antibody-adsorbent substrate with more of the antibody-resistant material to cover the bare surface of the substrate between the adsorbed antibody molecules.

54. The process of claim 53 wherein each antibody adsorbed in step C is delivered to its precise bare site on the antibody-adsorbent substrate by micropipetting.

55. The process of claim 53 wherein each antibody adsorbed in step C is delivered to its precise bare site on the antibody-absorbent substrate by an ink jet printer.

56. The process of claim 53 wherein the antibody-adsorbent substrate is composed of a hydrophobic material.

57. The process of claim 56 wherein the antibody-adsorbent substrate is composed of a hydrophobic, polymeric material.

58. The process of claim 57 wherein the antibody adsorbent substrate is composed of polystyrene, polypropylene, polyethylene, or copolymers of polypropylene and polyethylene.

59. The process of claim 58 wherein the antibody-adsorbent substrate is composed of polystyrene or polypropylene.

60. The process of claim 53 wherein the antibody-resistant material is bovine serum albumin, gelatin, lysozyme, octoxynol, polyoxyethylenesorbitan monolaurate, or a polyethylene oxide containing block copolymer surfactant.

61. The process of claim 60 wherein the antibody-resistant material is bovine serum albumin, gelatin, or lysozyme.

62. The process of claim 61 wherein the antibody-resistant material is bovine serum albumin.

63. A process for producing a multiple antibody patterned substrate comprising:

A. coating an antibody-adsorbent substrate with an antibody-resistant material that is resistant to the adsorption of antibodies;

B. removing portions of the antibody-resistant material by mechanical scribing using atomic force microscopy to produce bare sites on the antibody-adsorbent substrate having precise sizes and shapes and each site having a precise location which corresponds to a specific antibody;

C. adsorbing molecules of each antibody to its specific bare site on the antibody-adsorbent substrate;

D. rinsing the substrate to remove unadsorbed antibodies; and

E. coating the antibody-adsorbent substrate with more of the antibody-resistant material to cover the bare surface of the substrate between the adsorbed antibody molecules.

64. The process of claim 63 wherein each antibody adsorbed in step C is delivered to its precise bare site on the antibody-adsorbent substrate by micropipetting.

65. The process of claim 63 wherein each antibody adsorbed in step C is delivered to its precise bare site on the antibody-absorbent substrate by an ink jet printer.

66. The process of claim 63 wherein the antibody-adsorbent substrate is composed of a hydrophobic material.

67. The process of claim 66 wherein the antibody-adsorbent substrate is composed of a hydrophobic, polymeric material.

68. The process of claim 67 wherein the antibody adsorbent substrate is composed of polystyrene, polypropylene, polyethylene, or copolymers of polypropylene and polyethylene.

69. The process of claim 68 wherein the antibody-adsorbent substrate is composed of polystyrene or polypropylene.

70. The process of claim 63 wherein the antibody-resistant material is bovine serum albumin, gelatin, lysozyme, octoxynol, polyoxyethylenesorbitan monolaurate, or a polyethylene oxide containing block copolymer surfactant.

71. The process of claim 70 wherein the antibody-resistant material is bovine serum albumin, gelatin, or lysozyme.

72. The process of claim 71 wherein the antibody-resistant material is bovine serum albumin.

* * * * *

UNITED STATES PATENT AND TRADEMARK OFFICE
CERTIFICATE OF CORRECTION

PATENT NO. : 5,858,801
DATED : Jan. 12, 1999
INVENTOR(S) : ROBERT A. BRIZZOLARA

It is certified that error appears in the above-identified patent and that said Letters Patent is hereby corrected as shown below:

In the claims, claim 35, line 7, cancel "laser".

Signed and Sealed this

Twentieth Day of July, 1999

Attest:

Q. TODD DICKINSON

Attesting Officer

Acting Commissioner of Patents and Trademarks